United States Patent [19]

Coupal

[11] Patent Number: 4,513,607
[45] Date of Patent: Apr. 30, 1985

[54] ANALYTICAL FILTRATION TECHNIQUE

[76] Inventor: John Coupal, 329 Melbourne Way, Lexington, Ky. 40502

[21] Appl. No.: 313,231

[22] Filed: Oct. 20, 1981

[51] Int. Cl.³ .............................................. G01N 15/02
[52] U.S. Cl. ................................. 73/61.4; 73/432 PS; 210/927; 250/303
[58] Field of Search ................ 73/61.4, 61 R, 432 PS; 422/101, 71; 436/177, 57; 210/927, 446, 314, 318; 250/303

[56] References Cited

U.S. PATENT DOCUMENTS

| 3,749,556 | 7/1973 | Barak et al. | 250/303 X |
| 4,042,677 | 8/1977 | Molinski et al. | 250/303 X |
| 4,057,617 | 11/1977 | Abramovici et al. | 250/303 X |
| 4,066,742 | 1/1978 | Garrett | 250/303 X |
| 4,075,314 | 2/1978 | Wolfangel et al. | 250/303 X |
| 4,094,965 | 6/1978 | Layne et al. | 250/303 X |
| 4,401,566 | 8/1983 | Igari et al. | 210/927 X |

Primary Examiner—Donald O. Woodiel
Assistant Examiner—Joseph W. Roskos

[57] ABSTRACT

A procedure for accurately determining size distribution of macroaggregate and colloidal particles in a solution wherein the solution is passed through a first capillary filter of selected pore diameter and then through a tortuous path provided by a fibrous filter composed of fibers having affinity for the colloidal substance.

10 Claims, 1 Drawing Figure

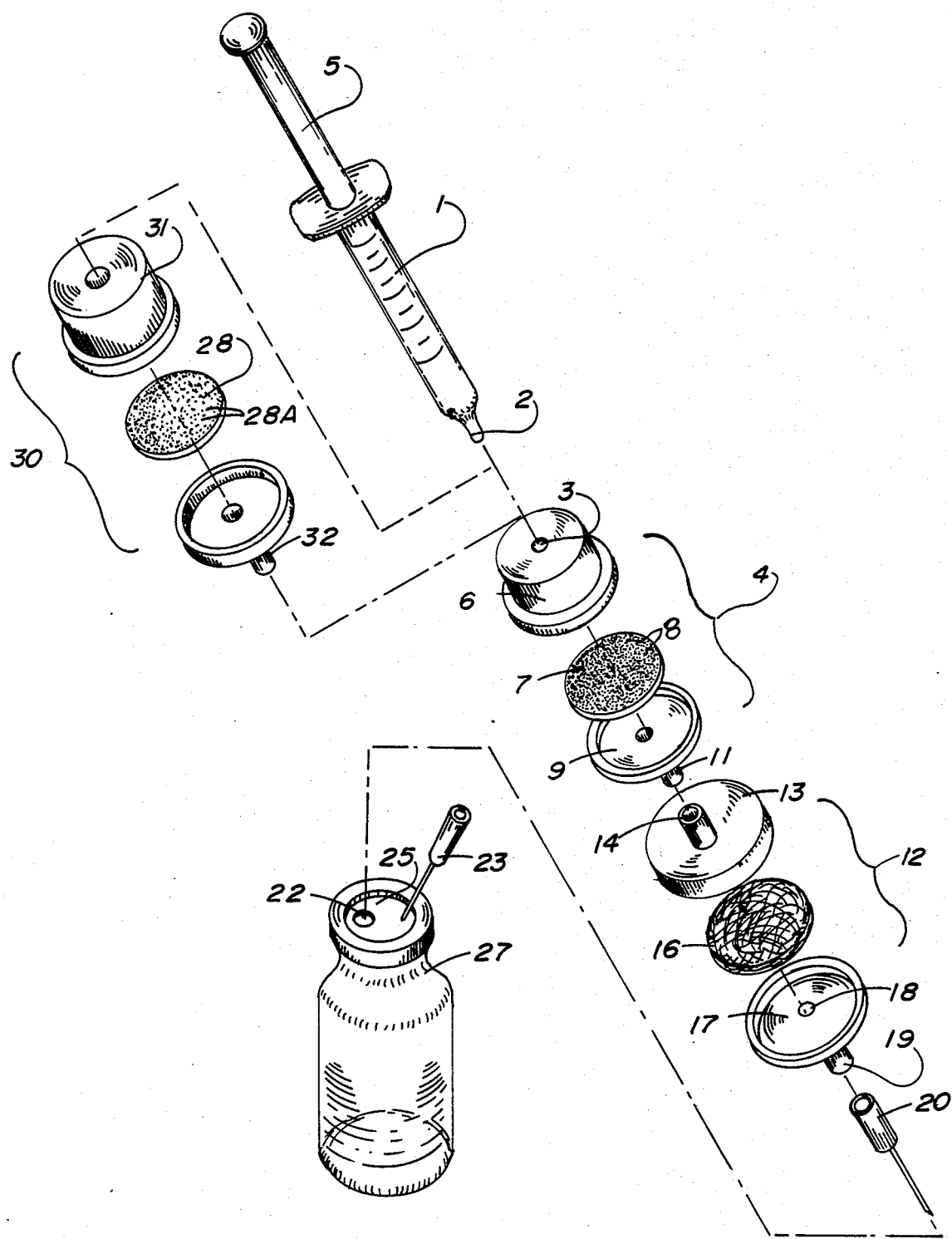

ANALYTICAL FILTRATION TECHNIQUE

BACKGROUND OF THE INVENTION

The present invention relates to a filtration procedure for assay of colloids in an aqueous colloidal suspension and is particularly useful as a quality control technique, for example to reveal radiochemical purity of colloids radiopharmaceuticals and thereby to indicate relative quality.

Such radiocolloids, for example colloids of Technetium-99m in liquid suspension, are used for liver and spleen function studies. After injection into the patient, the suspended particles are retained in the reticuloendothelial system to permit scintiphoto study of the liver, spleen, and bone marrow. However, particles larger than 8 micrometers cause difficulty by blocking capillaries of the lung producing interferring images of the lungs on the scintiphotos. In contrast, the radiochemical contaminate pertechnetate is soluable, passes through the reticuloendothelial system, but concentrates in the stomach. Interferring images of the stomach on the scintiphotos result. Therefore, qualification of pertechnetate and the larger particles of the suspension is important in the evaluation of study results.

Prior procedures for quality assessment of colloidal suspensions and particularly of radiocolloids by size classification have been tedious, time consuming and in some instances of questionable value.

In one prior art method serial stacked polycarbonate filters have been utilized where the polycarbonate filters are possessed with capillary openings of selected diameter so that the colloidal substance larger than the opening are retained at the opening while material of smaller diameter is passed to the next filter which has smaller diameter opening. In typical practice five units are utilized having diameters, respectively of 0.8, 0.6, 0.4, 0.2 and 0.08 micrometer.

Such arrangements to classify the size of colloidal particles require significant pressure to accomplish the classification. The use of the required pressure may cause (a) rupture of the filter or leakage around the filter, or (b) breakdown or deformation of the particles so the procedure yields results of questionable value.

Another, prior art method of determining quality control of radiocolloids is by Instant Thin Layer Chromatography Silica Gel (Gelman Sciences, Ann Arbor, Mich.) developed with sodium chloride 0.9% solution in water (i.e., normal saline). That method however, differentiates only radiocolloid (including larger particles) from pertechnetate.

It will be understood that, for the foregoing applications, and equally in other applications, classification analysis of the colloidal dispersion can be extremely important.

SUMMARY OF THE INVENTION

The present invention provides a new, useful and economical means for size classification of macroaggregate and colloidal particles in colloidal dispersions for example as an analytical or quality control procedure.

Method and apparatus within the scope of the present invention is particularly useful in the analysis or evaluation of radiocolloidal solutions and involves only a single-step filtration.

Moreover, method and apparatus within the scope of the present invention requires very little applied pressure to the material to be evaluated so that the character of the material, and particularly the colloidal particles is not affected as in previous methods so that the method and apparatus provided by the present invention yields more reliable evaluation data.

While the method and apparatus disclosed herein is discussed with reference to assay and evaluation of Technetium Tc-99m colloidal suspensions, it will be recognized that the method and apparatus is equally useful in other applications.

Briefly the present invention provides a procedure for accurately determining size distribution of macroaggregate and colloidal particles in a solution wherein the solution is passed through a first capillary pore filter of selected pore diameter and then through a tortuous path provided by a fibrous filter composed of fibers having affinity for the colloidal substance.

One example of a method and apparatus within the scope of the present invention is discussed with reference to the accompanying FIGURE but it will be understood that various modifications in application of the apparatus and method described herein, also within the scope of the present invention, will occur to those skilled in the art upon reading of the present disclosure.

BRIEF DESCRIPTION OF THE DRAWING

In the one accompanying FIGURE one example of an an apparatus is shown in exploded form for accomplishing the method of the present invention.

DETAILED DESCRIPTION OF THE DRAWING

The FIGURE presents an example of an apparatus within the scope of the present invention in exploded form.

A hypodermic syringe 1, for example a 5 milliliter disposable plastic hypodermic syringe by Becton, Dickinson Co., is provided. Syringe 1 is provided with a needle hub 2 to be sealably received in inlet 3 of a filter member 4, for example a "Pop-Top" membrane filter holder manufactured by Nuclepore Corporation of Pleasanton, Calif. Filter member 4 includes a top 6, which includes inlet 3, and contains a filter member 7 for example a 13 mm diameter polycarbonate filter membrane having pores 8 which in the present example can be 8 micrometer in diameter.

A bottom cover 9 is provided to be received by top 6 to provide a sealed unit so that fluid received by inlet 3 passes through membrane 7 for selective removal of particles having a diameter greater than 8 micrometer and the filtrate passes out of the unit by means of an outlet 11 of bottom cover 9.

A second filter unit 12 for example a Millex-GS filter unit is provided having a top cover 13 with an inlet 14 where outlet 11 of filter cover 9 is received in inlet 14.

Filter unit 12 also includes a bottom 17 with an outlet 18 communicating with a hub 19.

Filter 12 includes a membrane filter unit 16 for example a Millex-GS 0.22 micrometer mixed cellulose-esters manufactured by Millipore Corp, Bedford, Mass.

Similar components from other manufacturers can within the scope of the present invention be substituted for those previously recited.

It has been unexpectedly found that the arrangement previously recited accomplishes better results in terms of assay of colloidal suspension of Technetium-99m than obtained by prior art methods. Specifically, it has been found that by use of the membrane 16 of mixed cellulose esters the membrane provides a tortuous filter path and that the path in combination with the apparent affinity of the membrane for particles of the colloidal particles effectively removes particles having a diameter of 0.22 micrometer and smaller.

It is believed that the affinity of the membrane for the colloidal particles is by an adsorptive and/or absorptive phenomena.

As previously discussed one application of the method and apparatus in accordance with the present invention is particularly useful in assay of Technetium 99m radiocolloidal solution for liver, spleen, and bone marrow scanning procedures.

In this procedure the filter unit 4 traps particles which have the ability to block lung capillaries in humans while the particles having a diameter greater than and slightly less than 0.22 micrometer which pass through the lungs are trapped in filter unit 12 and those of significantly smaller diameter pass through the filter unit 12 to serum vial 27 where the filtrate is virtually all of the Technetium-99m pertechnetate. A needle 20 is provided on hub 19 and inserted through rubber septum 25 of vial 27. A vent needle 23 is also inserted through septum 25 for exhaust of displaced air.

In prior art methods the procedure has required the use of the stacked polycarbonate membranes and subsequent chromatographic analysis for pertechnetate quantification. The time consumed in the prior art method is greatly in excess of that required by the procedure of the present invention. Specifically, the present invention permits routine assay of a solution in terms of capillary occluding radio aggregates, pertechnate and the desired radiocolloid in a preparation of Tc-99m sulfur colloid, Tc-99m antimony sulfide colloid, or Tc-99m stannous colloid (i.e., reduced hydrolyzed technetium) before administration to a patient where the analysis requires less than 3 minutes. The results agree favorably with those obtained by the five-filter method or chromatography previously discussed.

PROCEDURE

The procedure and apparatus were evaluated for Technetium-99m sulfur colloid, Technetium-99m antimony sulfide colloid, or Technetium-99m stannous colloid (i.e., reduced hydrolyzed technetium) in comparison with the prior method as follows:

1. After gentle agitation of a vial of either Technetium Tc-99m-sulfur colloid, Technetium-99m antimony sulfide colloid, or Technetium-99m stannous colloid, the radiocolloid solution is drawn into a 5-milliliter disposable plastic hypodermic syringe fitted with needle to fill only the dead space of the syringe needle hub and needle (approximately 0.08 milliliters total volume).

2. The radiocolloid in the above syringe is diluted to 3.0 milliliters using sodium chloride solution (0.9%), U.S.P., from a flexible single-dose container with access at base for convenience.

3. With the needle in air, the plunger of the above syringe is pulled back to the 5-milliliter position to produce a 2-milliliter air pocket within the syringe barrel.

4. The syringe is swirled to mix the contents.

5. The needle is removed from the syringe, and the needle hub is fitted snugly into the upper female fitting (inlet) of the holder of the polycarbonate filter.

6. Gentle pressure is applied downward on the syringe plunger to force the liquid through both filters and into the vial. The air pockets permits clearance of as much liquid as possible from the polycarbonate filter unit and perhaps from the mixed-cellulose esters filter unit.

7. The filter units and filtrate unit are disassembled, and Tc99 m radioactivity counts per 0.5 minute are measured in each of the three components. The percentage of total measured radioactivity is computed for each of the individual filter units and for the filtrate. The percentage of radioactivity on the polycarbonate membrane filter unit indicates the percentage of radiocolloid dose which is capable of occluding lung capillaries. The percentage of radioactivity on the mixed cellulose esters filter unit indicates the percentage of desired radiocolloid. The percentage of radio activity in the filtrate is the radiochemical contaminate Tc-99m-pertechnetate.

The resulting mixtures were analyzed by determining radioactivity on the filters of the apparatus within the scope of the present invention and another sample of the same material analyzed by chromatography as in the prior art.

The results were as follows:

TABLE I

| RESULTS OF ASSAYS ON Tc-99m SULFUR COLLOID PREPARATIONS PERFORMED BY FILTRATION (INVENTION) AND BY CHROMATOGRAPHY | | | | | |
|---|---|---|---|---|---|
| | Techmetium-99m Macroaggregated | Technetium-99m Colloid | | Technetium-99m Pertechnetate | |
| | Invention | Chromatography | Invention | Chromatography | Invention |
| | 0% | 98.59% | 98.74% | 0.68% | 0.84% |
| | 0 | 98.70 | 98.07 | 0.61 | 0.48 |
| | 0.49 | 97.92 | 97.47 | 0.84 | 0.53 |
| | 0 | 98.78 | 97.76 | 0.26 | 0.75 |
| | 0.14 | 97.55 | 97.96 | 0.53 | 0.41 |
| | 0.11 | 98.07 | 97.74 | 0.21 | 0.63 |
| | 0.39 | 98.48 | 97.57 | 0.47 | 0.53 |
| | 0.62 | 98.29 | 97.34 | 0.33 | 0.53 |
| | 0.72 | 95.50 | 97.18 | 0.56 | 0.58 |
| MEAN | 0.32 | 97.98 | 97.60 | 0.50 | 0.67 |
| DIFFERENCE BETWEEN MEANS | | NOT SIGNIFICANT | | NOT SIGNIFICANT | |
| STANDARD DEVIATION | 0.31 | 0.96 | 0.66 | 0.19 | 0.28 |
| NUMBER PREPARATIONS | 10 | 10 | 10 | 10 | 10 |

TABLE II

RESULTS OF ASSAYS ON Tc-99m ANTIMONY SULFIDE COLLOID PREPARATIONS PERFORMED BY FILTRATION (INVENTION) AND BY CHROMATOGRAPHY

| | Techmetium-99m Macroaggregated | Technetium-99m Colloid | | Technetium-99m Pertechnetate | |
| --- | --- | --- | --- | --- | --- |
| | Invention | Chromatography | Invention | Chromatography | Invention |
| | 0% | 97.61% | 98.16% | 0.62% | 0.67% |
| | 0.7 | 97.84 | 96.70 | 0.74 | 0.56 |
| | 0 | 98.03 | 97.97 | 0.66 | 0.60 |
| | 1.08 | 98.22 | 96.38 | 0.70 | 0.51 |
| | 0 | 97.87 | 97.90 | 0.67 | 0.46 |
| MEAN | 0.36 | 97.91 | 97.42 | 0.68 | 0.56 |
| DIFFERENCE BETWEEN MEANS | | NOT SIGNIFICANT | | NOT SIGNIFICANT | |
| STANDARD DEVIATION | 0.50 | 0.23 | 0.82 | 0.04 | 0.08 |
| NUMBER PREPARATIONS | 5 | 5 | 5 | 5 | 5 |

TABLE III

RESULTS OF ASSAYS ON Tc-99m STANNOUS COLLOID PREPARATIONS PERFORMED BY FILTRATION (INVENTION) AND BY CHROMATOGRAPHY

| | Techmetium-99m Macroaggregated | Technetium-99m Colloid | | Technetium-99m Pertechnetate | |
| --- | --- | --- | --- | --- | --- |
| | Invention | Chromatography | Invention | Chromatography | Invention |
| | 0.56% | 89.80% | 96.74% | 1.93% | 0.10% |
| | 1.44 | 99.31 | 95.78 | 0.22 | 0.18 |
| | 0 | 99.86 | 97.56 | 0.03 | 0.06 |
| | 0 | 95.76 | 98.77 | 1.55 | 0.32 |
| | 0 | 99.66 | 97.64 | 0.12 | 0.34 |
| | 0.70 | 99.30 | 96.58 | 0.14 | 0.12 |
| MEAN | 0.45 | 97.28 | 97.18 | 0.66 | 0.19 |
| DIFFERENCE BETWEEN MEANS | | NOT SIGNIFICANT | | NOT SIGNIFICANT | |
| STANDARD DEVIATION | 0.58 | 3.97 | 1.04 | 0.84 | 0.12 |
| NUMBER PREPARATIONS | 6 | 6 | 6 | 6 | 6 |

In all cases the results were evaluated by recognized statistical method, (paired Student t test) and in all cases the mean differences were found to be not significant (probability ≧ 0.05).

In another procedure within the scope of the present invention where, for example, Technetium-99m macro-aggregated albumin or Technetium-99m Human Albumin Microspheres radiopharmaceuticals are to be evaluated it has been found that a porous filter of Teflon (TM E. I. DuPont, Co.) of selected pore size capillaries, for example 74 micrometer can be utilized prior to the filter unit 6 for determination of the concentration of over sized macroaggregates. In the example shown filter 28 is contained in a housing 30 similar to housing 6,9 previously described having an inlet 31 to receive needle hub 2 and an outlet 32 to be received in inlet 3 of top 6. The procedure used in this method is the same as previously discussed.

It will be understood that the apparatus and procedure within the scope of present invention previously described is not by way of limitation and that various other methods and apparatus also within the scope of the present invention will occur to those skilled in the art upon reading the disclosure set forth herein.

The invention claimed is:

1. A procedure for classifying macroaggregate and colloidal particles in a liquid dispersion by size wherein the dispersion is passed through a first capillary filter of selected pore diameter to retain particles and then through a tortuous path provided by a fibrous filter composed of fibers having affinity for the colloidal substance for removal of a portion of the colloidal particles and the balance of the particles are retained in the liquid passing through the first filter and the fibrous filler.

2. The invention of claim 1 wherein said dispersion includes colloidal technetium particles of random size distribution.

3. The invention of claim 1 wherein said fibrous filter includes fibers of cellulose esters.

4. The invention of claim 3 wherein said first capillary filter is a filter membrane of polycarbonate.

5. The invention of claim 4 wherein said colloidal dispersion includes radioactive sulfur compounds.

6. The invention of claim 4 wherein said colloidal dispersion includes radioactive antimony sulfide compounds.

7. The invention of claim 4 wherein said colloidal dispersion includes radioactive stannous compounds.

8. The invention of claim 1 wherein said dispersion includes albumin macroaggregate of random size distribution and wherein said procedure includes passing the portion of said dispersion through a second capillary filter having capillaries of larger diameter than of said first filter prior to passage of said solution through said first filter, for removal of particles of said albumin having selected diameter.

9. The invention of claim 1 wherein said dispersion is diluted with sodium chloride solution in a syringe, admitting a selected quantity of air to said syringe, and passing said dispersion through said first filter and fibrous filter followed by the air from said syringe and collecting the material emitted from the fibrous filter filtrate.

10. The invention of claim 9 including measuring the radioactivity of the material on the first filter, fibrous filter and filtrate.